United States Patent
De Rosa et al.

(10) Patent No.: US 9,630,954 B2
(45) Date of Patent: Apr. 25, 2017

(54) TCR/MHCII-COLLAGEN INTERACTION INHIBITORS USEFUL FOR TREATMENT OF RHEUMATOID ARTHRITIS

(71) Applicants: CONSIGLIO NAZIONALE DELLE RICERCHE, Rome (IT); UNIVERSITÀ CATTOLICA DEL SACRO CUORE, Milan (IT)

(72) Inventors: Maria Cristina De Rosa, Rome (IT); Francesco Ria, Rome (IT); Bruno Giardina, Rome (IT); Gianfranco Ferraccioli, Rome (IT); Davide Pirolli, Rome (IT); Chiara Nicolo', Sutri (IT)

(73) Assignees: Consiglio Nazionale delle Ricerche, Rome (IT); Università Cattolica del Sacro Cuore, Milan (IT)

( * ) Notice: Subject to any disclaimer, the term of this patent is extended or adjusted under 35 U.S.C. 154(b) by 0 days.

(21) Appl. No.: 14/389,759

(22) PCT Filed: Apr. 2, 2013

(86) PCT No.: PCT/IB2013/052623
§ 371 (c)(1),
(2) Date: Sep. 30, 2014

(87) PCT Pub. No.: WO2013/144931
PCT Pub. Date: Oct. 3, 2013

(65) Prior Publication Data
US 2015/0073030 A1    Mar. 12, 2015

(30) Foreign Application Priority Data

Mar. 30, 2012 (IT) .............. RM2012A0131

(51) Int. Cl.
| | | |
|---|---|---|
| *C07D 207/08* | (2006.01) |
| *C07D 401/04* | (2006.01) |
| *A61K 31/4025* | (2006.01) |
| *A61K 31/4439* | (2006.01) |
| *C07D 407/12* | (2006.01) |
| *A61K 31/343* | (2006.01) |
| *A61K 31/40* | (2006.01) |
| *A61K 31/403* | (2006.01) |
| *C07D 409/12* | (2006.01) |
| *C07D 207/06* | (2006.01) |
| *C07D 209/86* | (2006.01) |
| *C07D 209/88* | (2006.01) |
| *C07D 307/91* | (2006.01) |
| *C07C 251/86* | (2006.01) |
| *A61K 31/165* | (2006.01) |
| *A61K 31/381* | (2006.01) |

(52) U.S. Cl.
CPC .......... *C07D 407/12* (2013.01); *A61K 31/165* (2013.01); *A61K 31/343* (2013.01); *A61K 31/381* (2013.01); *A61K 31/40* (2013.01); *A61K 31/403* (2013.01); *A61K 31/4439* (2013.01); *C07C 251/86* (2013.01); *C07D 207/06* (2013.01); *C07D 207/08* (2013.01); *C07D 209/86* (2013.01); *C07D 209/88* (2013.01); *C07D 307/91* (2013.01); *C07D 401/04* (2013.01); *C07D 409/12* (2013.01); *C07C 2103/18* (2013.01)

(58) Field of Classification Search
CPC .. C07D 209/60; C07D 209/70; C07D 209/08; C07D 207/08; C07D 401/04; C09B 23/02; G01N 33/533; A61K 31/4025; A61K 31/4439
USPC ................ 548/427, 528; 514/411, 408, 343; 549/460; 546/276.4
See application file for complete search history.

(56) References Cited

U.S. PATENT DOCUMENTS

2009/0163545 A1    6/2009    Goldfarb

FOREIGN PATENT DOCUMENTS

WO    2008/064342    5/2008

OTHER PUBLICATIONS

STN Registry Database entry for CAS RN 1022920-30-4, Published in database on May 27, 2008.*
STN Registry Database entry for CAS RN 1025012-80-9, Published in database on Jun. 3, 2008.*
STN Registry Database entry for CAS RN 301160-21-4, Published in database on Nov. 3, 2000.*
STN Registry Database entry for CAS RN 400741-49-3, Published in database on Mar. 13, 2002.*
Ito et al. Cancer Science, (2003), 94(1), pp. 3-8.*
Tonkipii, V., A.B.Kosmachev, V.V.Petrov, E.A.Evdokimova, N.M. Libman, and S.M.Ramsh "The Synthesis and the m-Cholinolytic and Antihaloperidol Activities of Substituted Aminopentinols" Pharm. Chem. Journ. (2000), 34 (11), pp. 585-587.*
International Search Report for PCT/IB2013/052623, six pages, mailed Jan. 2, 2014.
Chemical Abstracts Service Database accession No. 518019-94-8, 9H-carbazole-9-propanoic acid, 3,6-diido-, 2-[(4-methylphenyl)methylene]hydrazide, one page (May 2003).
Chemical Abstracts Service Database accession No. 347369-28-2, 9H-carbazole-9-propanoic acid, 3,6-diido-, 2-[(4-hydroxyphenyl)methylene]hydrazide, one page (Jul. 2001).
Chemical Abstracts Service Database accession No. 342031-12-3, 9H-carbazole-9-propanoic acid, 3,6-dichloro-, 2-[(4-methylphenyl)methylene]hydrazide, one page (Jun. 2001).

* cited by examiner

Primary Examiner — Alicia L Otton
Assistant Examiner — Sagar Patel
(74) Attorney, Agent, or Firm — Nixon & Vanderhye PC

(57) ABSTRACT

The T cells specific to human collagen type II, one of the possible autoantigens, have a crucial role in the development of rheumatoid arthritis in the context of HLA-DR4. The protein-protein interactions between the T cell receptor (TCR) and the type II collagen linked to the allele MHC of class II HLA-DR4 may thus represent the target for the development of new drugs against rheumatoid arthritis. Using computational virtual screening techniques, families of pharmacologically active molecules have been identified that interfere with the TCR/collagen ll-MHCII interaction. The compounds identified here open up new possibilities in the treatment of rheumatoid arthritis.

10 Claims, 2 Drawing Sheets

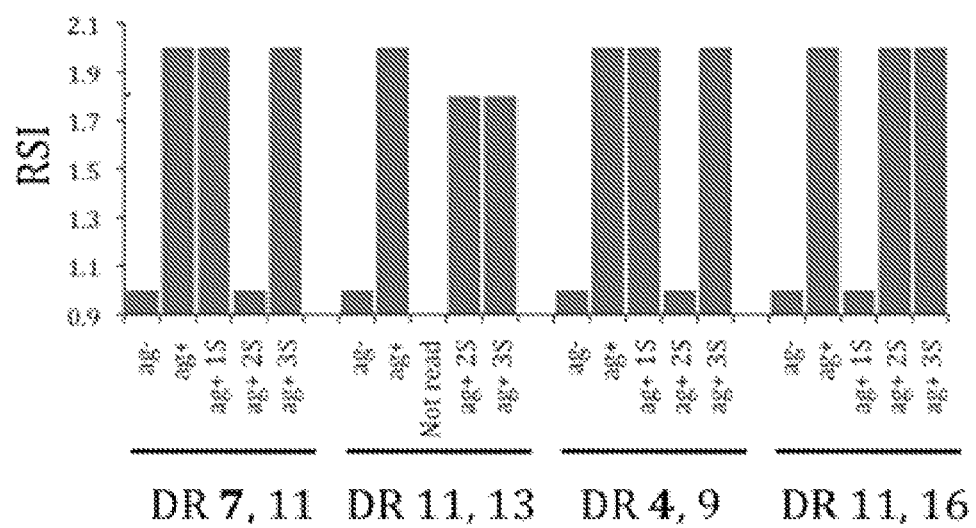
FIG: 1

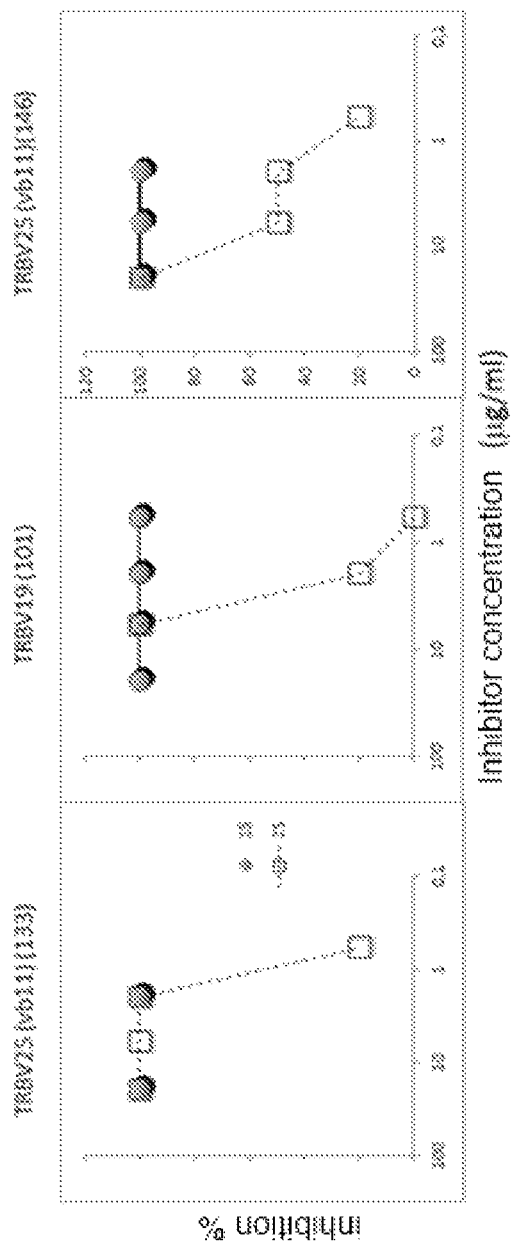
FIG: 2

TCR/MHCII-COLLAGEN INTERACTION INHIBITORS USEFUL FOR TREATMENT OF RHEUMATOID ARTHRITIS

This application is the U.S. national phase of International Application No. PCT/IB2013/052623, filed 2 Apr. 2013, which designated the U.S. and claims priority to Italian Application No. RM2012A000131, filed 30 Mar. 2012; the entire contents of each of which are hereby incorporated by reference.

STATE OF THE PRIOR ART

Rheumatoid arthritis (RA) is a chronic inflammatory disease that affects 0.5-1% of the population. It is a progressive disease that leads to the functional impotence of many joints. The etiology of the disease is unknown, but autoimmunity plays a dominant role in its pathogenesis. In fact, T cells and auto-antibodies are present in the blood of patients with RA. Most of the autoreactive T cells are specific to human collagen and can be found in inflamed joints where they promote the inflammatory response which ultimately leads to the destruction of cartilage. As confirmation of the role of T cells, RA has been demonstrated to be associated with the alleles HLA-DR 1 and 4. The present inventors have reported in the literature that it is possible to find T cells that are specific to human collagen type II in the context of HLA-DR4 in the blood and synovial fluid of patients, and the level of cells in the blood varies in parallel with the activity of the disease (Ria et al, Arth Res Ther 2008, 10: R135). Indeed, we have reported that the T cells specific to the peptide 261-273 of collagen type II (hu-Collp261) are present in large numbers in the blood at the onset of the disease, decreasing during the phases of clinical remission and increasing again at the time of relapses. A portion of these cells is spontaneously enriched in the synovial fluid during synovitis. From a methodological point of view, the method used allows to identify specific individual T cells through the identification of the sequence of the most variable region of the T cell receptor (TCR), the CDR3 region of the beta chain of the TCR, by PCR. The TCR recognizes the antigen to which it is specific as a complex of a peptide (in general comprised of length between 8 and 15 amino acids) with a molecule called HLA ("the peptide is presented by the HLA molecule to the TCR"). Each individual has between 12 and 20 of these molecules, each having its own chemical characteristics and each capable of binding a group of peptides which share the presence, in certain positions, of some amino acids. Each of the HLA molecules (which are coded in 6 different and contiguous gene loci on chromosome 6) has very wide genetic variability, with hundreds of alleles. The set of HLA molecules of an individual is called a haplotype. As mentioned above, in RA, 50% of patients have HLA-DR4 or DR1 in their haplotype. Both of these HLA molecules effectively present the peptide huCollp261. It should be added that the allele HLA-DR7 also presents the same type of peptides presented by HLA-DR4 and DR1. We estimate that about 70% of the T cells identified by the immunoscope technique in each patient are effectively specific to the complex DR4/huCollp261, on the basis of the fact that this is the fraction of cells that actually shares the use of common TCRs, this is the percentage of cells that proliferate only in response to this peptide and not in response to other control peptides (Ria et al Arth Res Ther 2008) and also based on the observation that this is the percentage of cells able to recognize this peptide in the context of another cross-reactive protein (unpublished observations). It should be highlighted, on the other hand, that also patients that are not positive for HLA-DR4, 1 or 7, may sporadically have the presence of cells that proliferate in response to the peptide huCollp261, but in this case this response is not related to the disease state. The use of the TCR sequences in the diagnosis and treatment of RA in these subjects was also the subject of a previous patent by F. Ria and G. F. Ferraccioli (RM2007A000429 and international PCT: PCT/IB2008/053152). The present inventors have subsequently described the three-dimensional interaction between the beta chain of the TCR and the complex formed by the human collagen peptide 261-273 (huCollp261) with HLA-DR4 (De Rosa et al, PloSOne 2010, 5:e11550), and this work forms the basis of the object of the present patent application. Since the etiology of RA is unknown, therapy has focused on the common pathogenic mechanism, i.e., inflammation. The current protocols of therapy include different types of medications: NSAIDs (nonsteroidal anti-inflammatory drugs), steroids and so-called DMARDs (disease-modifying anti-rheumatic drugs) which also include biological response modifiers, monoclonal antibodies capable of blocking TNF-α and IL-1, the major cytokines involved in the inflammatory response. Treatment in most cases includes the use of more than one of these drugs. Although therapy is effective in decreasing the severity of the disease, in the majority of cases the progression continues. In this regard, see the guidelines of the Italian Society of Rheumatology in *Clin Exp Rheumatol.* 2011 (3 Suppl 66):S7-14.—*Clin Exp Rheumatol.* 2011 (3 Suppl 66):S15-27.—*Clin Exp Rheumatol.* 2011 (3 Suppl 66):S42-62). In addition, these drugs can have serious side effects, generally proportional to their effectiveness, and often the treatment is followed by immunosuppression that allows the development of opportunistic infections or reactivation of latent infections that cause diseases such as tuberculosis and progressive multifocal leukoencephalopathy. Therefore there exists the need for new drugs that interfere more specifically with autoimmune response mechanisms, but that maintain the ability to control infectious agents.

Following an idea originally proposed in 1988 by L. Adorini, Liu Z, Li B, Li X, Zhang L, Lai L. published an article on the identification of molecules that inhibit the HLA-DR4-peptide interaction, entitled "*Identification of small-molecule inhibitors against human leukocyte antigen-death receptor 4 (HLA-DR4) through a comprehensive strategy*" *J. Chem Inf Model.* 2011 Feb. 28; 51(2):326-34. In this work scaffolds are identified for compounds capable of occupying the pocket of the HLA-DR4 molecule with greater affinity than other peptides that can be used for the same purpose. In order to apply this approach to RA therapy, the major limitation of these products is the need to block all HLA-DR4 molecules in order to obtain the desired therapeutic effect. The aforementioned article is irrelevant for the purposes of the present patent, since it has advantages of selectivity of the target and does not interfere with the recognition of the collagen by the T cells, but rather with the presentation of peptides in the context of HLA-DR4. In fact, to achieve a therapeutic effect with the products identified by Liu et al. the activity is also inhibited of all those T cells that recognize other peptides, derived from pathogens in complex with HLA-DR4. The objective of the product that we are presenting is to focus therapeutic intervention only on these complexes, thereby gaining advantages in terms of specificity, selectivity and pharmacological feasibility.

BRIEF DESCRIPTION OF THE INVENTION

The T cells specific to human collagen type II, one of the possible autoantigens, have a crucial role in the development of rheumatoid arthritis in the context of HLA-DR4. The protein-protein interactions between the T cell receptor (TCR) and the type II collagen linked to the allele MHC of class II HLA-DR4 thus represent the target for the development of new drugs against rheumatoid arthritis.

The present invention arises from the search for compounds capable of inhibiting the proliferation of T cells as a result of the interaction between the T cell receptor (TCR) and the type II collagen linked to allele HLA class II. Using PBMCs (Peripheral Blood Mononuclear Cells) of patients suffering from rheumatoid arthritis the possible toxicity of candidate inhibitors is first examined in vitro and subsequently, the ability is demonstrated of these inhibitors to specifically block the response to human collagen in the context of HLA-DR4 and the similar HLA-DR7.

Thus a family of molecules is identified that is able to selectively block only the immune response to the autoantigen, leaving the rest of the immune system intact and efficient.

Therefore the object of the invention are compounds with inhibiting activity of the interaction between the TCRs and the MHCII-Human collagen type II complex, or the MHCII complex and the antigenic peptide fragment in position 261-273 of human collagen type II (huCollp261), while they are irrelevant to the remaining functions of the immune system.

In particular the object of the present application are compounds having the general formula selected from the formulas (I), (II) and (III) for use in the treatment of RA.

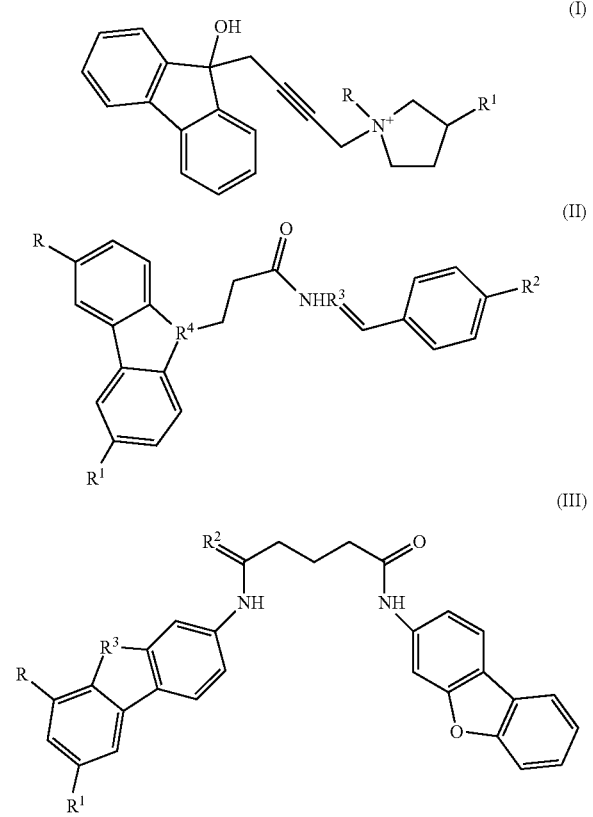

Making up part of the compounds of formula (I) is the new compound 9-[4-(3(R)-phenyl-1 (S)-propilpirrolidin-1-io-1-yl)but-2-ynyl]fluoren-9-ol and its analogues. Making up part of the compounds of formula (II) is the compound: (E)-3-(3,6-dichloro-9H-carbazol-9-yl)-N'-(4-hydroxy-benzylidene)propanidrazide and compounds of formula (III) the compound N1,N5-bis(dibenzo[b,d]furan-3-il)glutarammide (formula III).

The compounds of formula (II) and (III) have less inhibition activity than the compounds of formula (I), but are nevertheless usable in therapy.

Among these compounds, some have been synthesized for the first time by the present inventors. Therefore a second object of the invention are new compounds that fall under the generic formulas (I), (II) and (III).

A third object of the invention are the pharmaceutical compositions containing all of the compounds of formula (I), (II) and (III) and pharmaceutically acceptable excipients.

A fourth object of the invention is a method for preparing more effective compounds, of formula (I).

The compounds of the invention can be used advantageously in the therapeutic treatment, including symptomatic, of rheumatoid arthritis.

DESCRIPTION OF FIGURES

FIG. 1: The figure shows the results of a T cell proliferation test stimulated by the antigenic peptide 261-273 from human collagen (huCollp261). The test is performed in the absence of antigen (ag−), in the presence of antigen (ag+) and in the presence of ag+ and of a candidate inhibitor compound (2S,1S and 3S). The compound 2S, i.e. (9-[4-(3 (R)-phenyl-1(S)-propilpirrolidin-1-io-1-yl)but-2-ynyl]fluoren-9-ol) is capable of strongly depressing (about 100%) the Relative Stimulation Index (RSI) in the context of HLA-DR4 and HLA-DR7. The compound 1S (i.e. (E)-3-(3,6-dichloro-9H-carbazol-9-yl)-N'-(4-hydroxy-benzylidene) propanidrazide) strongly depresses (about 100%) the RSI in the context of HLA-DR11, while the compounds 2S and 3S, i.e., (N1,N5-bis(dibenzo[b,d]furan-3-yl) glutarammide), depress RSI less effectively, but nevertheless significantly (almost 20%), in the context of HLA-DR11.

FIG. 2: The figure shows the results of a T cell proliferation test obtained from a patient DR1+, stimulated by the antigenic peptide 261-273 from human collagen (huCollp261). The test is performed in the absence of antigen (ag−), in the presence of antigen (ag+) and in the presence of ag+ and of a candidate inhibitor compound (2S,1S).

DETAILED DESCRIPTION OF THE INVENTION

The compounds of the invention share the same pharmacological activity, namely the inhibition of the interaction between the TCRs and the MHCII-Human collagen type II complex, or the MHCII complex and the antigenic peptide fragment in position 261-273 of human collagen type II (huCollp261), despite being irrelevant to the remaining functions of the immune system.

Chemically the derivatives of the invention are molecules that share some biologically equivalent chemical structures such as the fluorine group, the carbazole group, dibenzofuran group and having the general formula selected from between formula (I), (II) and (III).

In particular the object of the invention are derivatives of 9-hydroxy fluorene of general formula (I)

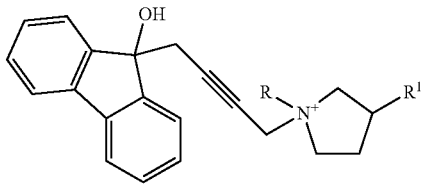

(I)

where R is a substituent selected from hydrogen, C1-C5 linear or branched alkyl, aryl-C1-C5-alkyl including halogen substituted on the phenyl group, and $R^1$ is a substituent selected from phenyl, halogen ortho-, meta- or para-substituted phenyl, where, in all cases, halogen is selected from chlorine, bromine or iodine, or $R^1$ is a group 2'- or 3'- or 4'-pyridyl.

In one embodiment of the invention, R is selected from hydrogen, a methyl group, ethyl, linear or branched propyl, linear or branched butyl, phenylethyl including substituted halogen ortho, for example o-chloro or o-iodo. R1 is selected among the groups: phenyl, 2'-pyridyl, 3'-pyridyl, 4'-pyridyl, o-iodophenyl, m-iodophenyl, p-iodophenyl, o-chlorophenyl, m-chlorophenyl, p-chlorophenyl.

Specific compounds of formula (I) are the compounds 1 to 15 below.

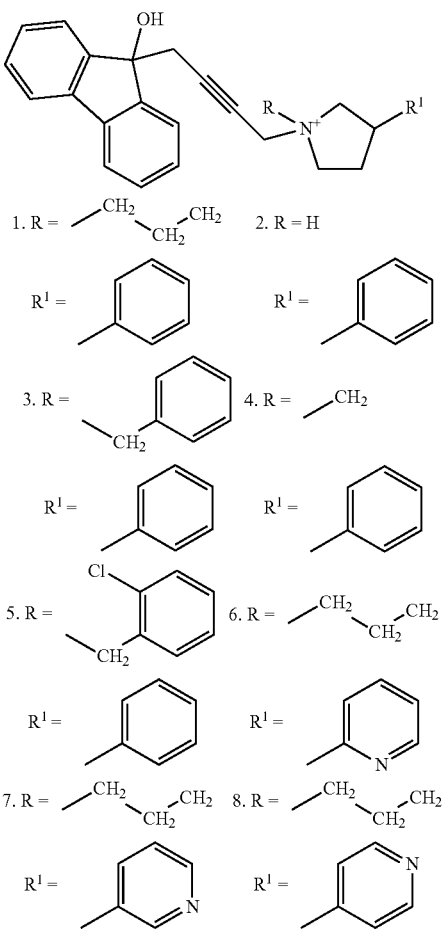

(I)

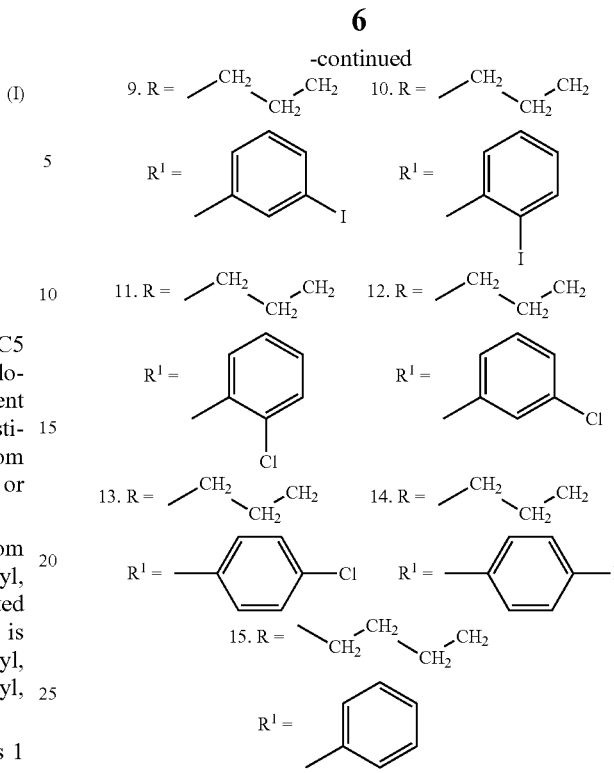

Among these, compound 1 is 9-[4-(3-phenyl-1-propilpirrolidin-1-io-1-yl)but-2-ynyl]fluoren-9-ol, in the form of a diastereoisomeric mixture.

All the compounds of formula (I) comprise two centers of asymmetry in positions 1 and 3 of the pyrrolidine group. An integral part of the present invention are diastereoisomeric mixtures (RR)/(SS) and (RS)/(SR) or individual racemic mixtures or individual enantiomers (RS), (SR), (RR), (SS). All the compounds of formula (I) may be in the form of ammonium salts, for example chloride, bromide, iodide.

The table below shows the binding affinity of the values of the individual stereoisomers of 9-[4-(3-phenyl-1-propilpirrolidin-1-io-1-yl)but-2-ynyl]fluoren-9-ol calculated by the molecular docking program AutoDock (Morris et al. J. Computational Chemistry, 19:1639-1662, 1998). These values are provided by the "scoring" function of the program. The docking process consists in virtually reproducing the association between a protein and a ligand by selecting the energetically favored complex, i.e. the one with the lowest interaction energy value (kcal/mol). The docking programs are characterized by the type of algorithm used and by the "scoring" function used. In a virtual screening the scoring functions are used to select the best conformation of the molecule within the site and, at the end of the process, to estimate the binding affinity of the complexes formed by the various candidate ligands.

| Compound | Binding affinity (kcal/mol) |
|---|---|
| 9-[4-(3(R)-phenyl-1(S)-propilpirrolidin-1-io-1-yl)but-2-inyl]fluoren-9-ol | −8.52 |
| 9-[4-(3(S)-phenyl-1(S)-propilpirrolidin-1-io-1-yl)but-2-inyl]fluoren-9-ol | −5.92 |
| 9-[4-(3(S)-phenyl-1(R)-propilpirrolidin-1-io-1-yl)but-2-inyl]fluoren-9-ol | −7.26 |
| 9-[4-(3(R)-phenyl-1(R)-propilpirrolidin-1-io-1-yl)but-2-inyl]fluoren-9-ol | −6.98 |

In particular, the preferred isomer of the compound 1 of Figure (I) is 9-[4-(3(R)-phenyl-1(S)-propilpirrolidin-1-io-1-yl)but-2-ynyl]fluoren-9-ol, which has the highest binding affinity, of all the compounds analyzed, to the T cell receptor (TCR) as highlighted by the lowest interaction energy (−8.52 kcal/mol).

Below are the binding affinities for all compounds of formula (I) calculated by the program AutoDock.

| Compounds of formula (I) | |
|---|---|
| Compound | Binding affinity (kcal/mol) |
| 1 | −8.52 |
| 2 | −8.37 |
| 3 | −8.31 |
| 4 | −8.27 |
| 5 | −8.09 |
| 6 | −7.59 |
| 7 | −8.21 |
| 8 | −6.67 |
| 9 | −8.47 |
| 10 | −6.33 |
| 11 | −7.48 |
| 12 | −6.17 |
| 13 | −8.51 |
| 14 | −7.66 |
| 15 | −7.24 |

In an alternative embodiment of the compounds of the invention are compounds with formula (II),

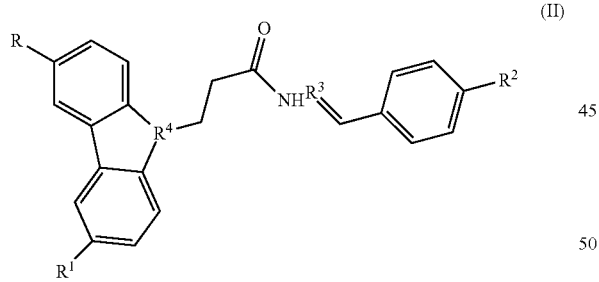

(II)

in which R is a substituent selected from hydrogen and halogen, selected from chlorine, bromine and iodine; $R^1$ is a substituent selected from hydrogen or halogen selected from chlorine, bromine or iodine; $R^2$ is a substituent selected from hydroxyl or C1-3 alkyl (methyl; ethyl, n-propyl, isopropyl); $R^3$ is a group selected from —N= and —CH= and $R^4$ is a group selected from N or CH.

The preferred compounds of formula (II) are the compounds 1 to 15 below, including the compound (E)-3-(3,6-dichloro-9H-carbazol-9-yl)-N'-(4-hydroxy-benzylidene) propanidrazide (compound 1).

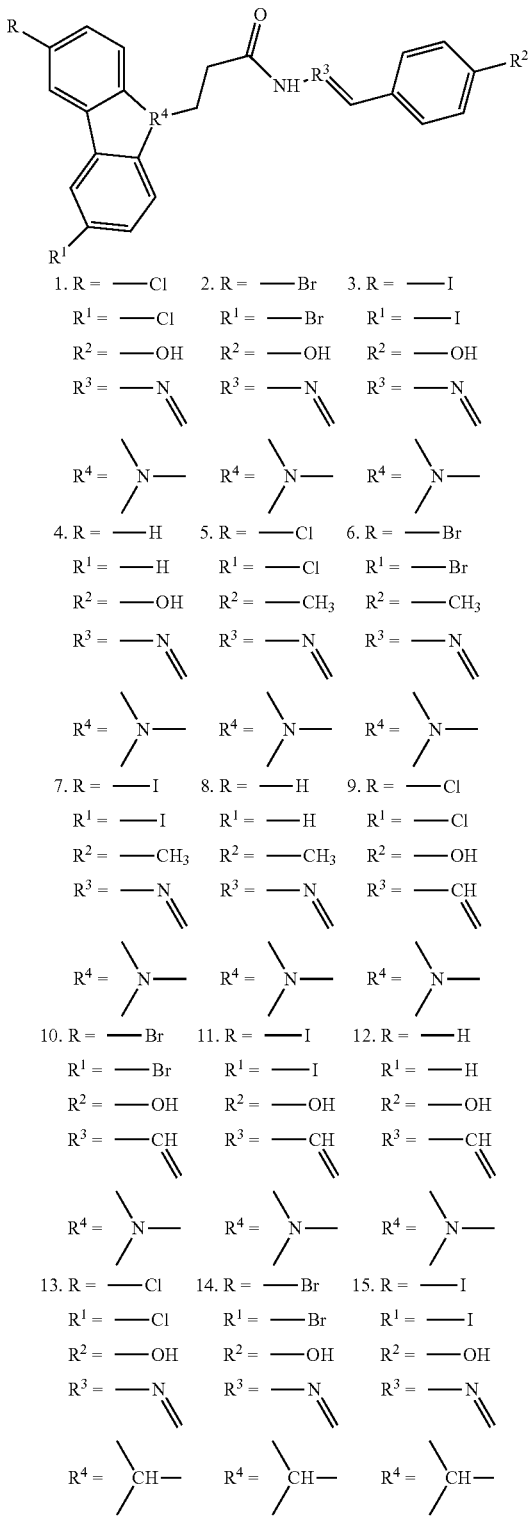

All the compounds of formula (II) may be in salt form on one of the nitrogen atoms, such as for example chloride, bromide, iodide.

In the case where $R^4$ is "=CH—" and R and $R^1$ are different, $R^4$ is a center of asymmetry. In this case, both the racemic mixture and the individual enantiomers (R) or (S) that separate a mixture enriched with one of the enantiomers are part of the invention.

Below are the binding affinities for all compounds of formula (II) calculated by the program AutoDock.

| Compounds of formula (II) | |
|---|---|
| Compound | Binding affinity (kcal/mol) |
| 1 | −7.82 |
| 2 | −5.57 |
| 3 | −6.34 |
| 4 | −7.59 |
| 5 | −7.44 |
| 6 | −7.23 |
| 7 | −7.59 |
| 8 | −7.76 |
| 9 | −7.80 |
| 10 | −6.24 |
| 11 | −5.83 |
| 12 | −7.29 |
| 13 | −7.23 |
| 14 | −6.01 |
| 15 | −6.07 |

In an alternative embodiment of the compounds of the invention are compounds with formula (III),

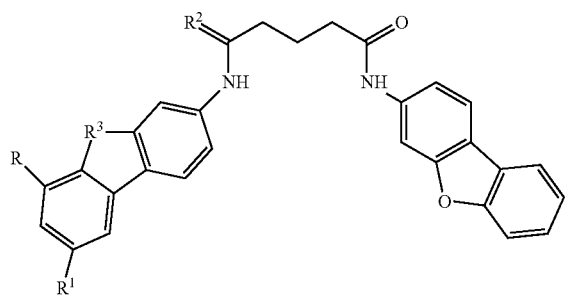

(III)

in which R is a substituent selected from hydrogen and halogen, selected from chlorine, bromine and iodine; $R^1$ is a substituent selected from hydrogen or halogen, selected from chlorine, bromine or iodine; $R^2$ is selected from O, NH, $CH_2$; $R^3$ is selected from O and S.

All the compounds of formula (III) may be in salt form on one of the nitrogen atoms, for example chloride, bromide, iodide. The preferred compounds of formula (III) are the compounds 1 to 15 below. The compound (1) is N1,N5-bis(dibenzo[b,d]furan-3-yl) glutarammide.

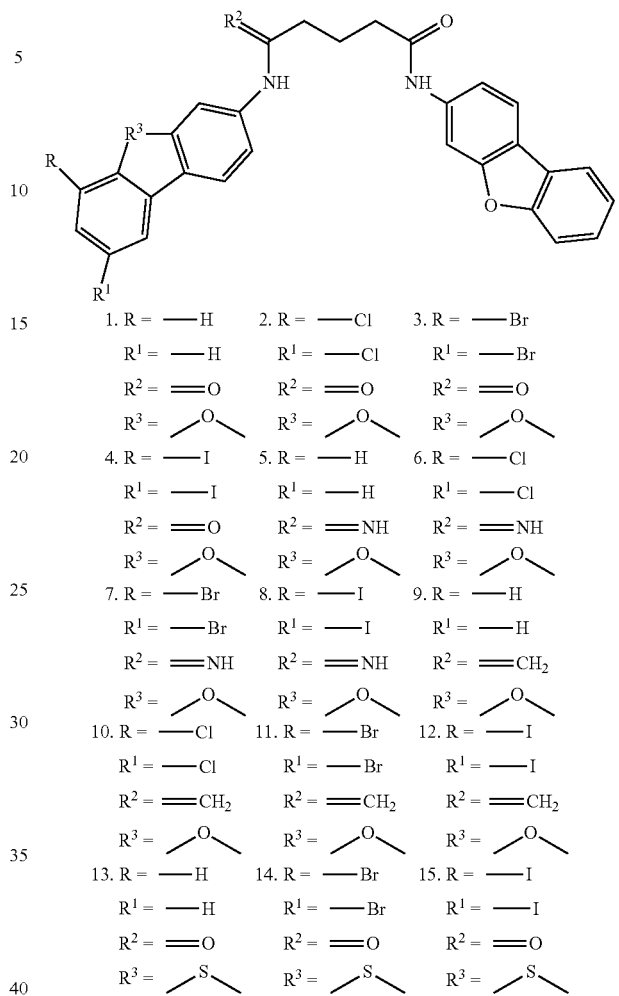

Below are the binding affinities for all compounds of formula (III) calculated by the program AutoDock.

| Compounds of formula (III) | |
|---|---|
| Compound | Binding affinity (kcal/mol) |
| 1 | −8.20 |
| 2 | −6.89 |
| 3 | −6.54 |
| 4 | −8.12 |
| 5 | −7.61 |
| 6 | −6.43 |
| 7 | −6.41 |
| 8 | −6.53 |
| 9 | −6.42 |
| 10 | −7.47 |
| 11 | −6.43 |
| 12 | −6.90 |
| 13 | −7.96 |
| 14 | −7.56 |
| 15 | −7.53 |

The compounds of the invention are identified and selected the first time through a "structure-based drug design" approach based on the three-dimensional structure of the ternary complex TCR/huColl261/HLA-DR4.

However, some of the compounds of the invention are commercially available through appropriate producers. In particular, the compound of general formula (I) molecule 1 can be purchased from the site www.ibscreen.com using the identification code: STOCK2S-15693, molecules 2-5 can be purchased online from the site www.molport.com using the respective identification codes: MolPort-001-993-760, Mol-Port-001-991-570, MolPort-002-558-653, MolPort-002-559-198.

For the compound of general formula (II), molecules 1, 4 and 8 can be purchased online from the site www.ibscreen.com using the respective identification codes: STOCK1S-19103, STOCK1S-01057 and STOCK3S-37745.

For the compound of general formula (III), molecule 1 can be purchased from the site www.ibscreen.com using the identification code: STOCK3S-02896.

All the known molecules can also be purchased from the companies: www.aurorafinechemicals.com, www.chemir.com, www.cyanta.com.

Unlike the previous compounds, compounds 6 to 15 of the General formula (I), compounds 2 and 3, from 5 to 7, from 9 to 15 of the General formula (II) and the compounds 2 to 15 of the general formula (III): are new compounds, synthesized by the present inventors. These compounds as such, their diastereoisomeric mixtures or conformational or racemic mixtures or isolated individual enantiomers, or their corresponding salts, are a further object of the present application.

All the compounds of formula (I) can be reproduced using the synthesis method shown schematically and described in example 1, which consists of steps and reactions that are in themselves well known and described in the literature. This method is exemplified in relation to the specific compound (1) in Formula (I), namely 9-[4-(3-phenyl-1-propilpirrolidin-1-io-1-yl)but-2-inyl]fluoren-9-ol.

All the compounds listed in Formula (I) can be synthesized by the same method using the corresponding acceptable intermediates.

In the case of the compounds of formula (I), the preparation method may include the additional step of resolution of the diastereoisomeric mixture (RR)/(SS) and (RS)/(SR) in the individual racemic mixtures or the separation of the individual enantiomers (RR), (SS), (RS) or (SR).

The separation can be performed using methods known to the expert, in which the separation is performed by zone electrophoresis (Capillary Zone Electropheresis CZE) using chiral selectors such as cyclo-dextrin.

The compounds of general formula (II) and (III) can also be synthesized according to methods known to the expert.

The object of the invention are also pharmaceutical compositions which contain one or more compounds of the invention as their active ingredient together with a pharmaceutically acceptable excipient and, optionally, common additives and stabilizers in the pharmaceutical industry.

Such compositions are suitable for local or systemic use and may be both in liquid formulation, solid, semi-solid, or suppository formulation.

Examples of liquid formulations are solution, suspension, emulsion, suitable e.g. for parenteral administration, local parenteral administration, oral administration or also in spray form. Examples of solid formulations are tablets, dragées, capsules, granules, freeze-dried tablets, that are suitable for oral administration. Examples of semi-solid formulations are pastes, salves, gels, ointments, that are suitable for topical application.

Each of these formulations shall contain a quantity of the active compound varying between 10 micrograms and 1000 mg, preferably between 100 micrograms and 100 mg, or between 100 micrograms and 50 mg, for example between 420 micrograms to 42 milligrams, for example 0.5, 1, 10, 30 mg per dosage unit (based on the concentrations used in toxicity tests).

Furthermore, the object of the present invention is also a method for preparing compounds of formula (II) comprising at least one of the steps listed in the following scheme 2

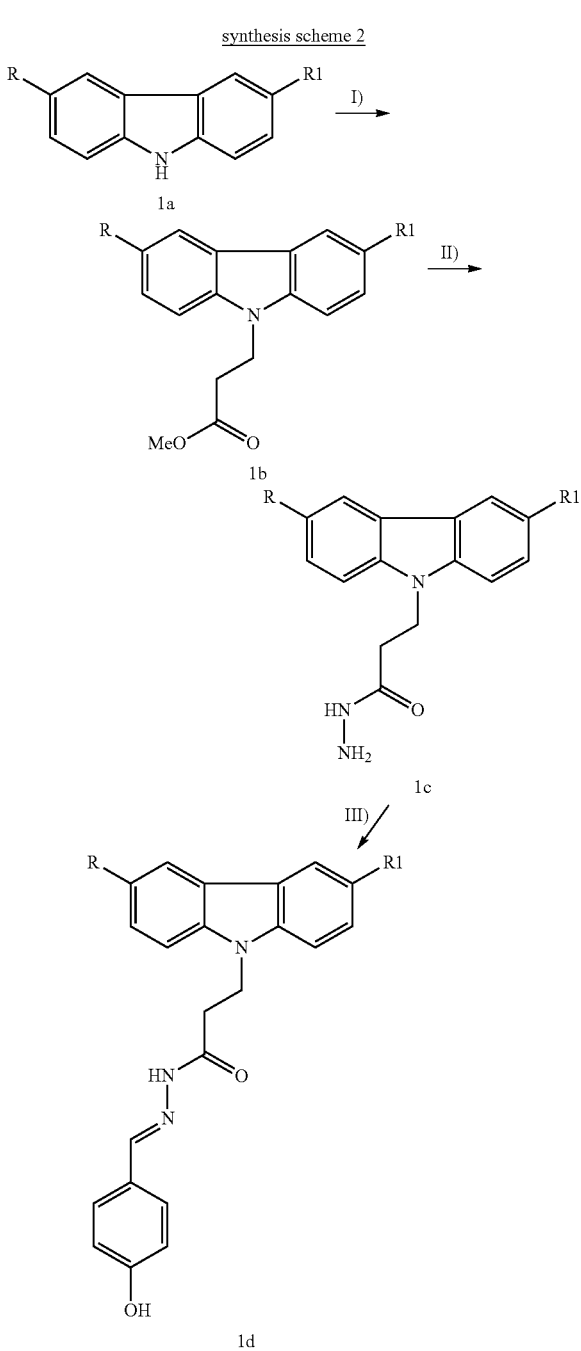

The experimental work underlying the present invention has allowed for the selection of molecules capable of partially inhibiting or totally blocking the proliferation of T cells caused by the presence of the corresponding antigen: in this case caused by human collagen type II, and more precisely its antigenic fragments, such as the fragment 261-273 (huCollp261). Partial inhibition is defined as any degree of inhibition less than 100%, between 10% and 99%, e.g. 20%, 30%, 40%, 50%, 60% 70%, 80%.

The relevant observations are shown in FIG. 1 and Table I in example 2. In the experiment shown in FIG. 1, PBMCs from four patients (one DR4+, one DR7+ and two negative for the HLA-DR alleles associated with RA) are cultured in the absence or presence of huCollp261 (10 microM) and in the latter case also in the presence of each of the three candidate inhibitors (I)-1 (2S), (II)-1 (1S) and (III)-1 (3S) at the same concentration. The results clearly indicate how 2S is able to block the proliferation of the cells that respond to huCollp261 in DR4+ or DR7+ subjects. In agreement with the observation that these compounds are free of toxic effects at concentrations up to 100 microM, the proliferation of sporadic T cells that respond to the same peptide, but in the context of HLA molecules different from DR4 1 or 7, remains intact. In the experiment shown in Table I, we examined the ability of 1S, 2S and 3S to inhibit the proliferation of T cells specific to huCollp261 in a greater number of DR4 patients. In total, we examined 4 DR4+ patients and observed the responses of 15 different T cells. The compound 1S inhibits 13% of these cells, 2S inhibits 60% and 3S inhibits 45%, indicating that all three compounds possess inhibitory activity. It is important to note that the three compounds have inhibitory activity on the same group of T cells; in other words the cells inhibited by 1S are also inhibited by 2S and 3S, and the cells inhibited by 3S are also inhibited by 2S. This indicates that all three compounds have the same mechanism of action although they are not structurally identical. Finally it is stressed that the cells inhibited by 2S are also the ones capable of cross-recognition of the peptide (see above).

Without wishing to limit the invention to specific scientific theory, it is believed that the inhibition of T cell proliferation by the compounds of the invention is the consequence of inhibitory interference on the mechanisms of interaction between T cell receptors (TCR) and the HLA DR-Collagen complex.

This hypothesis is supported by the following observations: 1. The compounds do not exhibit toxicity on PBMCs, 2. Although the compounds are not structurally identical, they inhibit the proliferation of cells functionally belonging to the same group, indicating that the mechanism that underlies the inhibition is the same; 3. The T cells that are subject to the inhibitory action are the same that have the ability to cross-recognize the peptide of other origin. Therefore the action of the compounds is specifically limited to a homogeneous group of T cells that share the molecular basis of recognition of the complex huCollp261 in complex with HLA-DR4, DR1 and DR7. In addition, the molecular modeling data do not convincingly demonstrate that the compounds act by blocking the binding pocket of the HLA molecule for the peptide huCollp261.

Therefore it can be reasonably stated that the molecules of the invention selectively block only the immune response of the autoantigene, i.e. peptide 261-273 of Human type II collagen, leaving the rest of the immune system intact and efficient.

The concentrations of the compounds tested for toxicity are of the order of micromoles/l. For example, 1, 5, 10, 20, 50, 100 micromoles/l. The concentration tested for the activity is about 10 micromoles/l.

The experimental results demonstrate that the molecule (2S): 9-[4-(3-phenyl-1-propilpirrolidin-1-io-1-yl)-but-2-inyl]fluoren-9-ol completely blocks the proliferation of T cells specific to the collagen fragment huCollp261 in the context of DR4 (FIG. 1), that the molecule (1S): (E)-3-(3,6-dichloro-9H-carbazol-9-il)-N'-(4-hydroxy-benzylidene) propanidrazide) strongly depresses RSI (about 100%) in the context of HLA-DR11, while the compounds 2S (above) and 3S: N1,N5-bis(dibenzo[b,d]furan-3-yl) glutarammide, suppress the proliferation of T cells in the context of DR11 in a statistically significant manner, albeit less effectively.

The invention will be illustrated below in detail in the following examples, which are by way of example, but not limiting.

EXAMPLES

Example 1: Synthesis of Compound 9-[4-(3(S)-phenyl-1(S)-propilpirrolidin-1-io-1-yl)but-2-inyl]fluoren-9-ol The synthesis is carried out according to scheme 1 below:

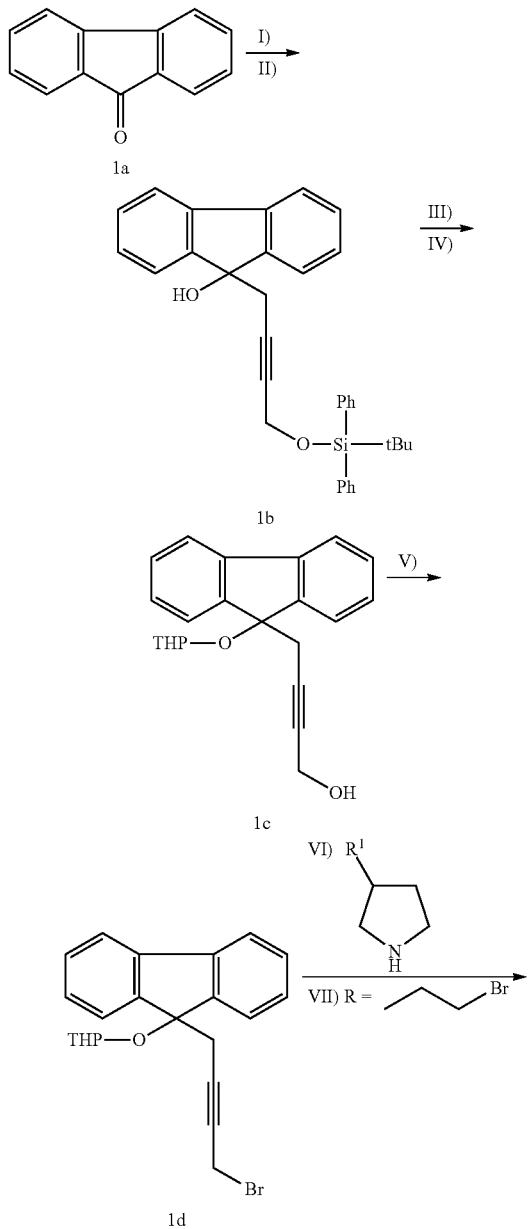

synthesis scheme 1

-continued

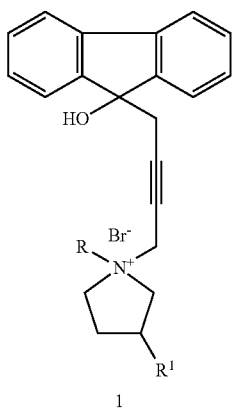

I) The compound 1a (3 g, 1.66·10⁻² mol), commercially available, is dissolved in Et₂O (diethyl ether) (250 ml). To it is added an ether solution of t-BuPh₂SiOCH₂CCCH₂MgBr (bromide of {4-[(tert-Butyl-diphenylsilyl)-oxy]-2-butyn-1-yl}magnesium), (1.66·10⁻² mol in 250 ml) (Tetrahedon Letters 1993, 5467).

II) The solution of NH₄Cl (ammonium chloride) is added, stirred for 15 minutes and then extracted with AcOEt (ethyl acetate). The organic phase is concentrated under vacuum and purified by gravity chromatography [silica gel, CHCl₃ (chloroform)-MeOH(methanol) (98:2)]. Product 1b is obtained with a yield of 70%.

III) To a solution of 1b (5.67 g, 1.162·10⁻² mol) and PPTS (pyridinium p-toluenesulfonate) (0.117 g, 4.6·10⁻⁴ mol) in CH₂Cl₂(dichloromethane) (500 ml), a solution of DHP (dihydropyran) (3.2 ml, 3.5·10⁻² mol) is added dropwise. The reaction is left under stirring at room temperature for 4 h, washed with a saturated solution of NaHCO₃ (sodium bicarbonate) and extracted with CH₂Cl₂.

The organic phase is anhydrified with Na₂SO₄ (sodium sulfate), filtered and concentrated under vacuum.

IV) The crude is dissolved in anhydrous THF (tetrahydrofuran). This solution is brought to a temperature of 0° C., TBAF (tetrabutylammonium fluoride) is added (2.63 g, 1.3·10⁻² mol) and it is put under stirring at room temperature for 45 min. The resulting mixture is diluted with CH₂Cl₂ and quenched with H₂O (water).

The organic phase is washed with brine (saturated solution of sodium chloride), anhydrifed with Na₂SO₄ and concentrated under vacuum.

V) To a solution of compound 1c (3.88 g, 1.162·10⁻² mol) and Et₃N (triethylamine) (4.8 ml, 3.2·10⁻² mol) in anydrous THF (500 ml), PBr3 (phosphorus tribromide) is added (1.5 ml, 1.162·10⁻² mol) at a temperature of −20° C. The reaction is left under stirring at room temperature for 4 h after which H₂O is added. The mixture thus obtained is extracted with AcOEt. The organic phase is washed with brine (saturated solution of sodium chloride), anhydrifed with Na₂SO₄ and concentrated under vacuum. The crude is purified by gravity chromatography [silica gel, Hexane-EtOAc (70:30)]. Product 1d is obtained with a yield of 50%.

VI) To a solution of compound 1d (2.3 g, 5.8·10⁻³ mol) and Et₃N (0.725 ml, 1.16·10⁻² mol) in anydrous THF (380 ml), compound 3 (0.848 g, 5.8·10⁻³ mol) is added (Khimiko-Farmatsevticheskii Zhurnal, 25(4), 60-2; 1991) at a temperature of −20° C. The reaction is left under stirring at room temperature for 4 h after which H₂O is added. The mixture thus obtained is extracted with AcOEt. The organic phase is washed with brine (saturated solution of sodium chloride), anhydrifed with Na₂SO₄ and concentrated under vacuum.

VII) The crude is dissolved in hot THF and to the solution is added n-PrBr (0.528 ml, 5.8·10⁻³ mol) (propyl bromide). The reaction is left to reflux for 2 h and concentrated under vacuum.

VIII) The crude is solubilized in THF dry, the solution is brought to 0° C., acidified with AcOH 1M (acetic acid) and left under stirring for 3 h at room temperature. The solution is concentrated under vacuum.

Example 2: Synthesis of Compound ((E)-3-(3,6-dichloro-9H-carbazol-9-yl)-N'-(-4-hydroxy-benzylidene)propanidrazide Synthesis scheme 3

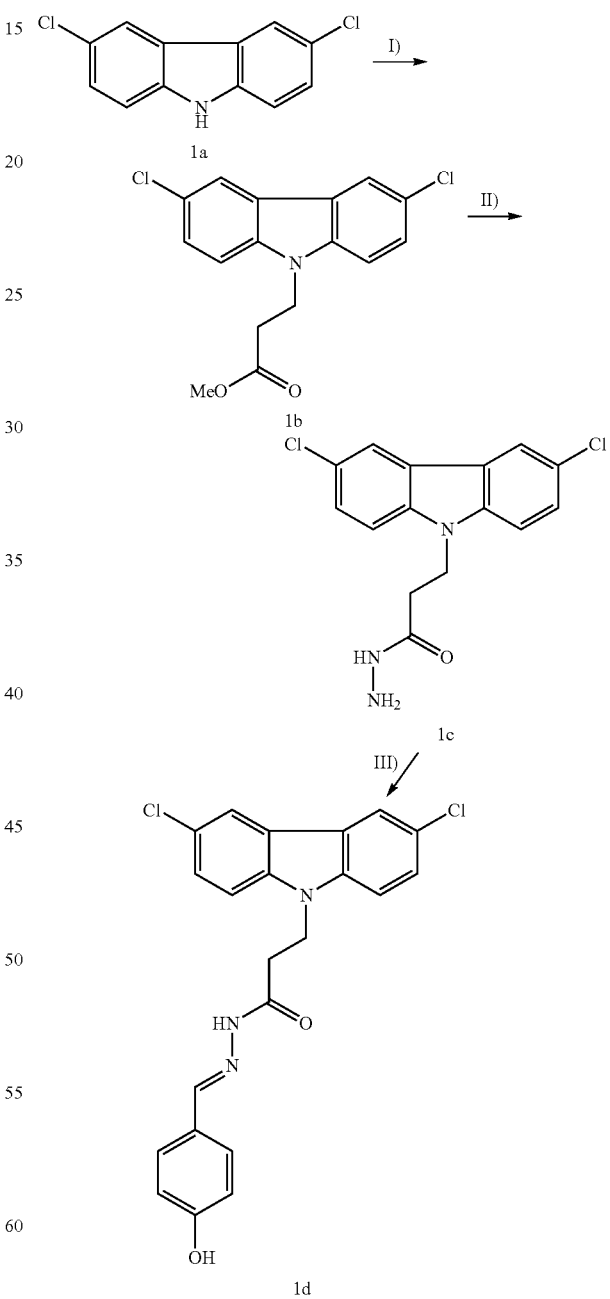

I) A solution of 3,6-dichloro-9H-carbazole (compound 1a), commercially available, (1.06 g, 4.5 mmol) and methyl acrylate (0.45 mL, 5 mmol) in acetic acid is left under stirring for 24 hours in a closed tube at a temperature of 90° C. The reaction mixture is purified in water and ice, basified with Na2CO3 and extracted in dichloromethane. The organic extracts are washed with a saturated solution of Na2CO3, dried over Na2SO4, and concentrated at reduced pressure. The residue is purified by flash chromatography (SiO2, eluting in gradient from hexane to hexane/EtOAc 8:2) to yield compound 1b, methyl3-(3,6-dichloro-carbazol-9-yl) propionate (1.28 g, 88%).

II) A solution of 1b (1.28 g, 3.96 mmol and hydrazine hydrate sol. 50% (0.25 mL, 4 mmol) in ethanol is heated to reflux and left under stirring for 6 hours. The solvent is removed at reduced pressure. The compound 1c, 3-(3,6-dichloro-carbazol-9-yl)-propionic acid hydrazide is obtained in quantitative yield without further purification.

III) A solution of 1c (1.28 g, 3.96 mmol) e 4-hydroxy-benzaldehyde (484 mg, 3.96 mmol) in ethanol is heated to reflux and stirred for 12 hours. Then the solvent is removed at reduced pressure. The reaction crude is redissolved in ethyl acetate and washed with HCl 1N and with brine (saturated aqueous solution of NaCl). The organic phase is dried over Na2SO4, and concentrated at reduced pressure. The residue is crystallized from a mixture of EtOAc/petroleum ether 40:60 to give a crystalline solid of compound 1 d, (4-hydroxy-benzylidene)-hydrazide (E)-3-(3,6-dichloro-carbazol-9-yl)-propionic acid (1.5 g, 90%).

Analogous synthetic procedure can be used for the compounds with formula (II) 2,3,4, using 3,6-dibromo-9H-carbazole, 3,6-diiodo-9H-carbazole and 9H-carbazole as starting product, respectively.

Example 3: Synthesis of the Compound 3S
(N1,N5-bis(dibenzo[b,d]furan-3-yl) glutarammide

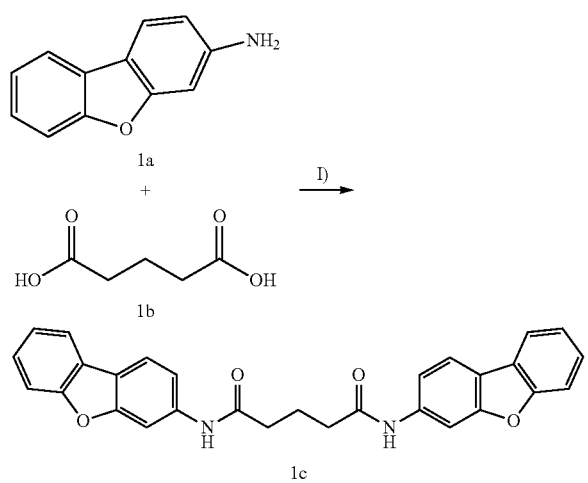

I) In a flask are introduced 366 mg of 1a (3-amminodibenzofuran, 2.0 mmol), 1b (132 mg of glutaric acid, 1.0 mmol), 135 mg of HOBT (1.0 mmol), 10 ml of dichloromethane and 0:14 ml of triethylamine (1.0 mmol). The solution is cooled to 0° C. with an ice bath and 206 mg of DCC is added (1.0 mmol). It is left under stirring for 15 minutes and then the ice bath is removed. After a short time a white precipitate of cyclohexylurea forms, it is left under stirring for another 3 h, then filtered on gooch and the solvent is evaporated at reduced pressure. The crude is purified by column chromatography (eluent EtOAc: hexane 25:75), the pure product 1c is obtained with a yield of 80%.

For the synthesis of the other derivatives it is sufficient to work in excess of glutaric acid in such a way as to isolate the mono-amidified product. Then we proceed with the next reaction in the same conditions but using a 3-amminodibenzofuran or an appropriately substituted 3-aminodibenzothiophene.

Example 4: T Cell Proliferation Test for DR4+ and DR7+ Patients

Mononuclear cells (PBMCs, Peripheral Blood Mononuclear Cells) are isolated from four patients with rheumatoid arthritis using a density gradient. One patient is DR4+, one DR7+ (DR4, DR7 and DR1 present the same peptides and the response to human collagen peptide 261-273 restricted by these alleles use the same TCRs); two patients are negative for DR4, DR1 or DR7. The PBMCs are cultured at a concentration of 5×106 cells/ml in 24-well plates in RPMI 1640 medium supplemented as described (Arth Res Ther, 2008) without (ag−) or with the antigenic peptide (10 μg/ml, ag+) or with the same concentration of peptide in the presence of an equimolar concentration of the commercial diastereoisomeric mixture of 9-[4-(3-phenyl-1-propylpyrrolidin-1-ium-1-yl)but-2-ynyl]fluoren-9-ol (2S) comprising the active enantiomer 9-[4-(3(R)-phenyl-1(S)-propylpyrrolidin-1-ium-1-yl)but-2-ynyl]fluoren-9-ol, in a final volume of 1 ml. After three days, the cells are collected and the "immunoscope" analysis is performed as previously described. This analysis allows for the identification of T cells that proliferate in response to the antigen. This proliferation is referred to as RSI (specific stimulation index) with a value of 1 corresponding to the non-stimulated sample. The graph (FIG. 1) shows the ability of 9-[4-(3-phenyl-1-propilpirrolidin-1-io-1-yl)but-2-inyl]fluoren-9-ol to block the proliferation of the T cells that respond to the presence of the antigenic peptide 261-273 (huCollp261) only in the context of HLA-DR4 or DR7 that broadly share the ability to bind peptides.

While limited to this experiment the two other molecules tested (1S and 3S) show more modest inhibition capacity and specificity, in an experiment performed on a larger group of patients, the results of which are reported in Table I, 1S and 3S also show a significant ability to inhibit the proliferation of T cells specific to Type II collagen in the DR4+ context.

TABLE I

PBMC from 4 patients with RA HLA-DR4+ are stimulated with huCollp261 in the presence of each of the 3 compounds that are the object of this patent.

| Compound | Number of specific T cells | Number of cells inhibited | % |
| --- | --- | --- | --- |
| 1S | 15 | 2 | 13 |
| 2S | 15 | 9 | 60 |
| 3S | 11* | 5 | 45 |

*in one patient it is not possible to test this compound due to the insufficient number of cells obtained from sampling.

Example 4: Test for Proliferation of T Cells in DR1+ Patients

Three types of T cells specific to huCollp262 (TRBV25 (133), TRBV19 (101) and TRBV25 (146)), obtained from a patient Dr1+ DR4−, are subjected to a proliferation test conducted as described in the previous example 2. In particular, the test is performed in the absence of antigen (ag−), in the presence of antigen (ag+) and in the presence of ag+ and of a candidate inhibitor compound (1S and 2S). The results are expressed as a % of inhibition of T cell expansion (TRBV25 (133), TRBV19 (101) and TRBV25 (146)) in the absence of inhibitor, at the indicated concentrations of the two inhibitors. As shown in FIG. 2, the compound 1S, i.e. ((E)-3-(3,6-dichloro-9H-carbazol-9-yl)-N'-(4-hydroxy-benzylidene) propanidrazide) is able to strongly depress (about 100%) the Rate of Specific Stimulation (RSI) of T cells in the DR1+ patient, in two cells out of three at a concentration 10 times lower than the compound 2S (9-[4-(3(R)-phenyl-1(S)-propilpirrolidin-1-io-1-yl)but-2-ynyl]fluoren-9-ol). These data demonstrate therefore that the compound 1S is a specific inhibitor of the recognition of collagen II, also in the context of DR1+.

human collagen type II or an antigenic fragment thereof, and a pharmaceutically acceptable excipient; wherein said inhibitor is a compound of formula (I):

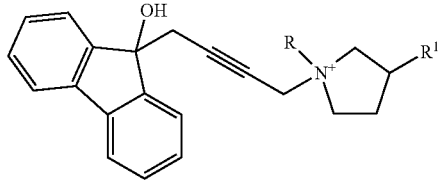

wherein R is selected from the group consisting of hydrogen, a methyl, ethyl, n-propyl, iso-propyl, n-butyl, iso-butyl, tert-butyl, phenylethyl group, and substituted o-chloro, o-bromo or o-iodo forms thereof; R1 is selected from the group consisting of: phenyl, 2'-pyridyl, 3'-pyridyl,

---

---

The invention claimed is:

1. A method for treating rheumatoid arthritis, comprising administering an inhibitor of interaction between T cells and a complex of MHC-II and human collagen type II or an antigenic fragment thereof to a patient who is HLA-DR4 positive, HLA-DR7 positive, or both HLA-DR4 positive and HLA-DR7 positive; wherein said inhibitor is a compound of formula (I):

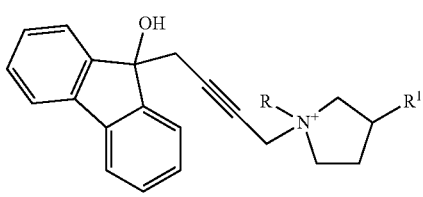

wherein R is selected from the group consisting of hydrogen, a methyl, ethyl, n-propyl, iso-propyl, n-butyl, iso-butyl, tert-butyl, phenylethyl group, and substituted o-chloro, o-bromo or o-iodo forms thereof; R1 is selected from the group consisting of: phenyl, 2'-pyridyl, 3'-pyridyl, 4'-pyridyl, o-iodophenyl, m-iodophenyl, p-iodophenyl, o-chlorophenyl, m-chlorophenyl, and p-chlorophenyl; and is in the form of a diastereoisomeric mixture, racemic mixture, isolated enantiomer, or salts thereof.

2. A method for treating rheumatoid arthritis, comprising administering a pharmaceutical composition; wherein said composition includes, as active ingredient, an inhibitor of interaction between T cells and a complex of MHC-II and 3. The method according to claim 1, wherein said antigenic fragment of human collagen type II is the peptide 261-273 (SEQ ID NO: 1).

4. The method according to claim 1, wherein said inhibitor is selected from the group consisting of compounds 1 to 15 of formula (I)

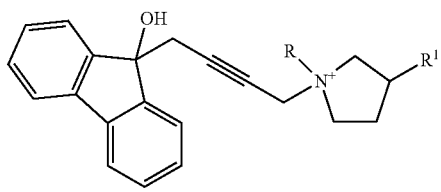

-continued

5. R = 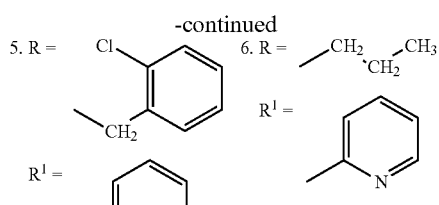

6. R = 
R¹ =

7. R = 8. R = 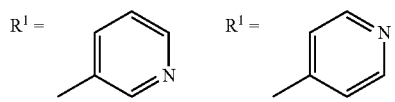

9. R = 10. R = 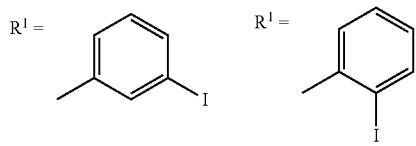

11. R = 12. R = 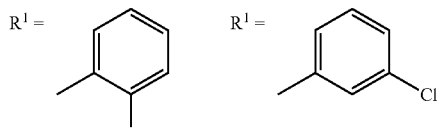

13. R = 14. R = 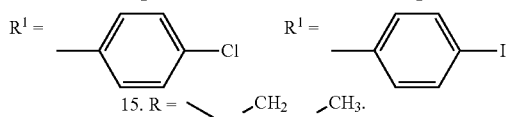

15. R = 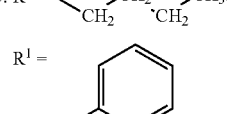
R¹ = 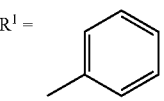

5. The method according to claim 1, wherein said inhibitor is 9-[4-(3(R)-phenyl-1(S)-propilpirrolidin-1-io-1-yl)but-2-ynyl]fluoren-9-ol or a salt thereof.

6. The method according to claim 1, wherein said inhibitor is of general formula (I)

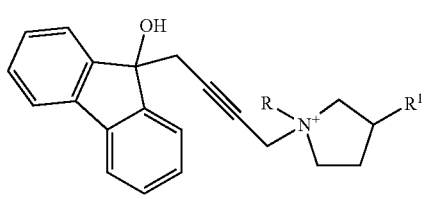

in the form of a diastereoisomeric mixture (RR)/(SS) or (RS)/(SR); of an individual racemic mixture; an individual enantiomer (RS), (SR), (RR), or (SS); or a salt thereof selected from the group consisting of:

6. 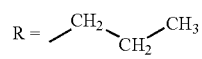
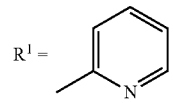

7. 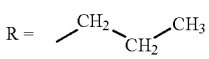
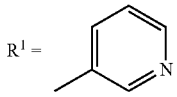

8. 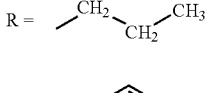
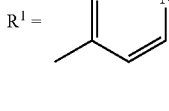

9. 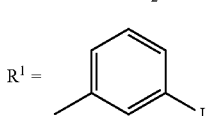
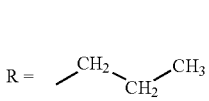

10. 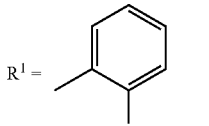
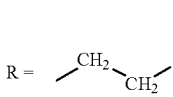

11. 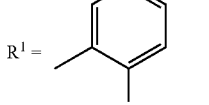
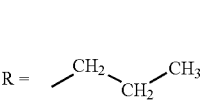

12. 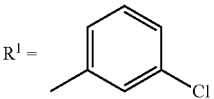

13.

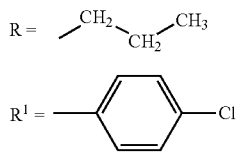

14.

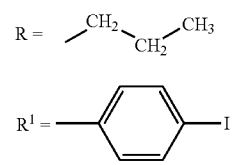

15.

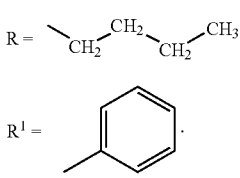

7. The method according to claim 2, wherein said antigenic fragment of human collagen type II is the peptide 261-273 (SEQ ID NO: 1).

8. The method according to claim 2, wherein said inhibitor is selected from the group consisting of compounds 1 to 15 of formula (I)

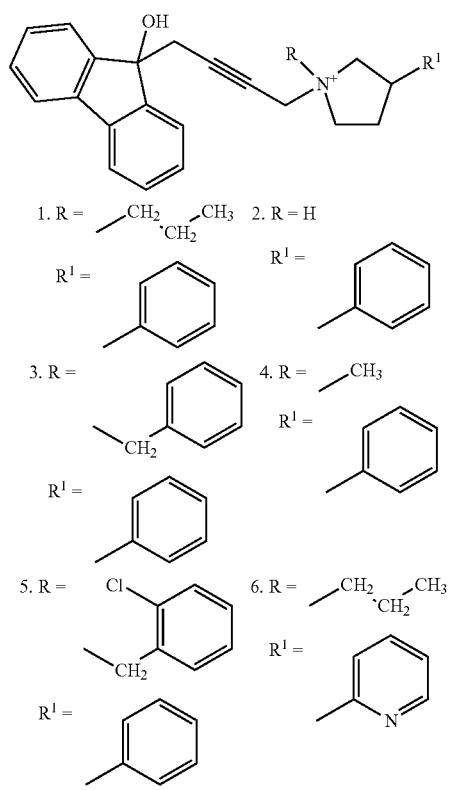

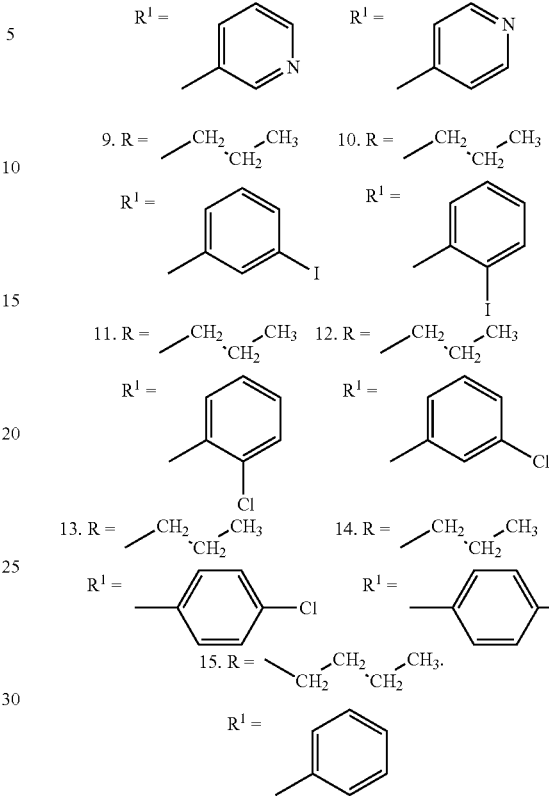

9. The method according to claim 2, wherein said inhibitor is 9-[4-(3(R)-phenyl-1(S)-propylpirrolidin-1-io-1-yl)but-2-ynyl]fluoren-9-ol or a salt thereof.

10. The method according to claim 2, wherein said inhibitor is of general formula (I)

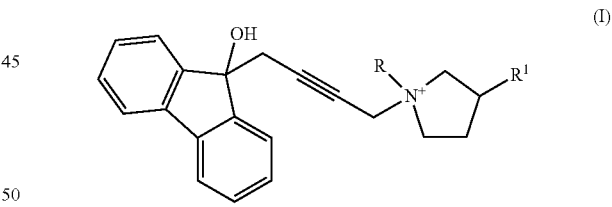

in the form of a diastereoisomeric mixture (RR)/(SS) or (RS)/(SR); of an individual racemic mixture; an individual enantiomer (RS), (SR), (RR), or (SS); or a salt thereof selected from the group consisting of:

6.

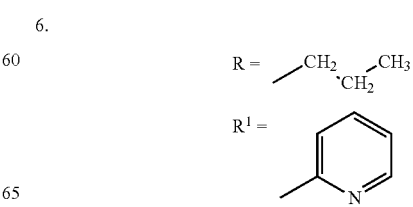

-continued
7.
R = 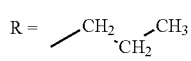
R¹ = 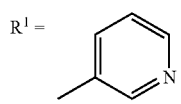
8.
R = 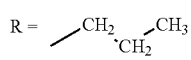
R¹ = 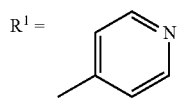
9.
R = 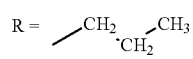
R¹ = 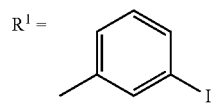
10.
R = 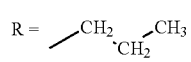
R¹ = 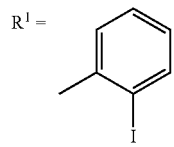
11.
R = 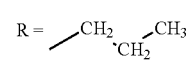
R¹ = 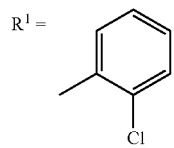
-continued
12.
R = 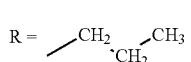
R¹ = 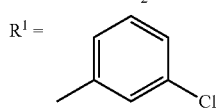
13.
R = 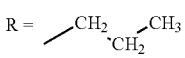
R¹ = 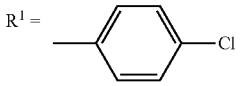
14.
R = 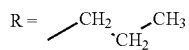
R¹ = 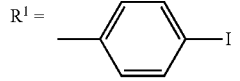
15.
R = 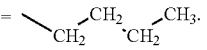
R¹ = 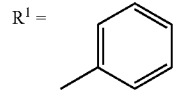
* * * * *

SEQUENCE LISTING

<160> NUMBER OF SEQ ID NOS: 1

<210> SEQ ID NO 1
<211> LENGTH: 13
<212> TYPE: PRT
<213> ORGANISM: Homo sapiens

<400> SEQUENCE: 1

Gly Lys Ala Gly Glu Arg Gly Pro Pro Gly Pro Gln Gly
1               5                   10